US006702988B1

(12) United States Patent
Sagona et al.

(10) Patent No.: US 6,702,988 B1
(45) Date of Patent: Mar. 9, 2004

(54) AUTOMATIC ON-SITE DRUG TESTING SYSTEM AND METHOD

(76) Inventors: Peter J. Sagona, 161 Ridgeview Dr., Pottstown, PA (US) 19465; David P. O'Bryan, 110 Stone Pine Dr., Kennett Square, PA (US) 19116

(*) Notice: Subject to any disclaimer, the term of this patent is extended or adjusted under 35 U.S.C. 154(b) by 0 days.

(21) Appl. No.: 09/295,853

(22) Filed: Apr. 21, 1999

(51) Int. Cl.[7] .............................................. G01N 33/48
(52) U.S. Cl. ........................ 422/61; 422/58; 422/82.05; 436/165; 436/169; 436/816; 436/901
(58) Field of Search ............................... 422/56, 58, 61, 422/82.05; 436/43, 46–47, 106, 164, 165, 169, 816, 817, 901

(56) References Cited

U.S. PATENT DOCUMENTS

| | | | |
|---|---|---|---|
| 461,126 A | | 10/1891 | Collins |
| 3,601,119 A | | 8/1971 | Engelsher |
| 3,982,898 A | | 9/1976 | McDonald |
| 4,094,020 A | | 6/1978 | Franklin |
| 4,244,920 A | | 1/1981 | Manschot et al. |
| 4,361,537 A | | 11/1982 | Deutsch et al. |
| 4,473,530 A | | 9/1984 | Villa-Real |
| 4,519,248 A | | 5/1985 | Torii et al. |
| 4,700,714 A | | 10/1987 | Fuisz |
| 4,774,192 A | * | 9/1988 | Terminiello et al. .......... 422/56 |
| 4,799,928 A | | 1/1989 | Crowley |
| 4,923,438 A | | 5/1990 | Vasconcellos et al. |
| 5,281,395 A | * | 1/1994 | Markart et al. .......... 422/82.05 |
| 5,403,551 A | | 4/1995 | Galloway |
| 6,097,831 A | * | 8/2000 | Wieck et al. ................ 382/128 |
| 6,249,593 B1 | * | 6/2001 | Chu et al. .................... 382/128 |
| 6,342,183 B1 | | 1/2002 | Lappe et al. |

FOREIGN PATENT DOCUMENTS

| | | |
|---|---|---|
| EP | 0 908 724 | 4/1999 |
| GB | 1 574 864 A | 9/1980 |
| GB | 1 574 864 | 9/1980 |
| WO | WO 98/38917 | 9/1998 |
| WO | WO 00/46598 | 8/2000 |

OTHER PUBLICATIONS

International Search Report for International Application No. PCT/US00/10963 dated Oct. 9, 2000.
Warren, Gorham & Lamont, "On–Site Drug Tests Evaluated," Substance Abuse Report, ISSN 1040–4163, vol. XXX, No. 6, Mar. 15, 1999.
Ultrak, BC460 1/3 Black & White Board Camera on sale Jun. 1, 1995.
Escreen™ Automated Point of Service System, SmithKline Beecham Clinical Laboratories Automation Lab No date.
BioScan Screening Systems, Inc., "Rapid Drug Screen" No date.
BioScan Screening Systems, Inc., "AdultaCheck™4" No date.
SUR–SCAN, "The Rapid Drug Screen™" (1999) No date.

\* cited by examiner

*Primary Examiner*—Lyle A. Alexander
(74) *Attorney, Agent, or Firm*—RatnerPrestia

(57) ABSTRACT

A system and method for on-site drug testing rapidly and objectively performs a drug screen on a urine sample at a collection center. The system includes a plurality of collection centers, wherein each collection center includes a test station for performing the drug testing. The test station includes collection cups for holding urine samples, test kits which couple to the collection cups in a fixed position, and an automatic reader which holds the collection cups and test kits in a fixed position under a predetermined level of illumination and produces an electronic image of the test kit. The test station also includes a computer workstation and a bar-code reader. The computer workstation generates electronic test order forms and receives image data from the automatic imaging system to evaluate the test results as indicated on the test kits. The bar-code reader is used to enter bar-code information which associate the collection cups and the test kits with the respective people being tested. The automatic reader reads and interprets the results. All results are sent to a central location.

9 Claims, 5 Drawing Sheets

AUTOMATIC ON-SITE DRUG TESTING SYSTEM AND METHOD

FIELD OF THE INVENTION

The present invention relates to the field of drug testing. More specifically, the present invention concerns a system and method of performing on-site drug testing using a test kit, a sample collection cup and an automated reader to read and interpret the test results and to transmit the results to a central location.

BACKGROUND OF THE INVENTION

Testing for the presence of controlled substances has been widely used in government and industry for more than fifteen years. The traditional testing method involves collection of a urine sample from a donor, then sending the sample to a central laboratory for testing. A qualitative screening test is performed on the sample—the results of all of the tested samples are reported to the client, although negative results are often reported earlier than positive or inconclusive results. If a test is positive, it is repeated and the results are evaluated by a neutral third party. The target turn-around time for reporting negative results is 24 hours. There are many factors, however, such as sample transport time, lab staffing and daily volume fluctuations that can delay results. Approximately 85–90% of the samples tested for drugs screen negative. There is an industry need to obtain results from negative drug screens more quickly.

In response to this industry need, manufacturers have developed drug screening tests that can be evaluated at the collection sites. Many on-site test kits are designed to work on urine samples. The kit consists of one or more test strips packaged in a plastic housing. Typically, a technician applies a small amount of a urine sample (e.g. three drops) to a predetermined area on the test kit. The urine is then conveyed through the test strip, for example, by capillary action. Certain areas on the test strip are reactive when brought in contact with a specific drug analyte (e.g., Cocaine, THC, PCP). This reaction causes a change in the appearance of the test strip in that local area. The test strips also include a control area which indicates that the urine has been conveyed to all of the test areas and, thus, provides an indication of when the results of the test may be read. After this area indicates a completed test, the technician reads the test strip and reports the result.

With on-site testing, negative drug screens can be reported to the client in a shorter time period than for laboratory tests. There is a growing interest in the use of on-site testing in the retail industry for pre-employment screening. While these on-site test kits have gained widespread use, they are not without problems. First, the indicator for the drug analyte relies on a chemical reaction which may produce a continuum of results depending on the batch from which the test strip was selected, the age of the test strip and what the person being tested ate or drank before being tested. These variations in the indicators may result in one technician reading a result as a negative while another tester would read the same result as being inconclusive. Because all inconclusive tests must be followed up with a laboratory test and that test evaluated by an independent third party, it would be beneficial if a test could be devised which did not rely on human judgement or on the training or experience of the technician administering the test.

Finally, many test kits require the technician to measure a predetermined amount of urine and apply it to the test kit. This may undesirably bring the technician into contact with the urine.

SUMMARY OF THE INVENTION

The present invention is embodied in an on-site drug test system that can rapidly perform a drug screen on a fluid sample. The system includes a central database and a plurality of remote collection centers, wherein each collection center includes a test station for performing the drug testing, each test station includes collection cups, test kits, a bar code scanner, includes an automated reader, and a computer workstation.

The present invention is embodied in a method for conducting an on-site drug test in which a donor provides a fluid sample and a technician inoculates a test kit. An automated reader takes an image of the test kit and then automatically interprets and records the results. All results are sent to a central location. Samples, corresponding to tests which are either indeterminate or positive, are sent to a central laboratory for confirmatory testing.

It is to be understood that both the foregoing general description and the following detailed description are exemplary, but not restrictive, of the invention.

BRIEF DESCRIPTION OF THE DRAWING

The invention is best understood from the following detailed description when read in connection with the accompanying drawing. Included in the drawing are the following Figures.

DETAILED DESCRIPTION OF THE INVENTION

Although the present invention is described in terms of a test kit which tests urine samples, it is contemplated that it may be extended to cover the automatic evaluation and reporting of test results based on other bodily fluids (e.g. saliva) or other aspects of a person which may indicate possible drug use such as a donor's sweat, hair or breath.

An exemplary on-site drug testing system according to the present invention includes the following components:

A network of collection sites.

Integrated consumables—the on-site test kit and the urine collection container that work together. Each of the consumables is given a bar-code which is associated with the person being tested.

An automated test strip reader that eliminates the subjective nature of manual reads and transposition errors when recording results.

A computer workstation which allows a minimally skilled technician to automatically generate test orders, record the chain of custody for the samples and transmit the on-site results to a central database.

Figure 1:
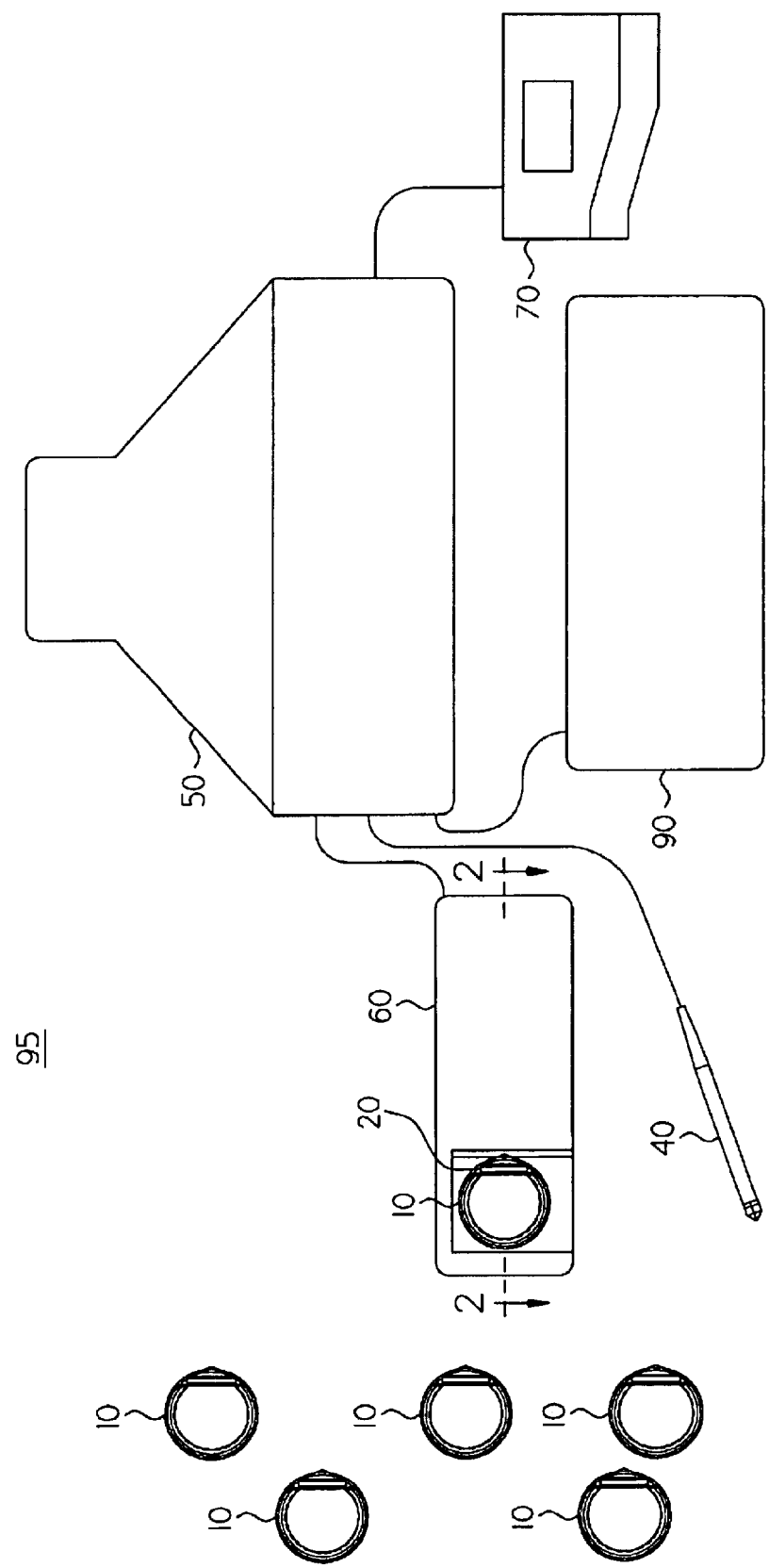
FIG. 1 is a top plan view of a test station showing some of the components of the on-site drug testing system.

FIG. 1 shows an exemplary collection site, including several components for the on-site drug testing system. The arrangement on table 95 includes, an automated reader platform 60, a computer workstation 50, which includes a CPU, a modem, a monitor and a keyboard 90, an automated signature reader 70, a bar code scanning wand 40 and a plurality of collection cups 10. Referring to FIG. 1, one of the collection cups 10 is placed onto the reader 60. The collection cup 10 contains one of the test kits 20. Keyboard 90 is used by the technician to enter appropriate information on the person being tested. The wand 40 is used to scan the bar code or codes of the test kit, sample vial (not shown) and the collection cup to associate a particular sample and test result with a particular individual.

Figure 2:
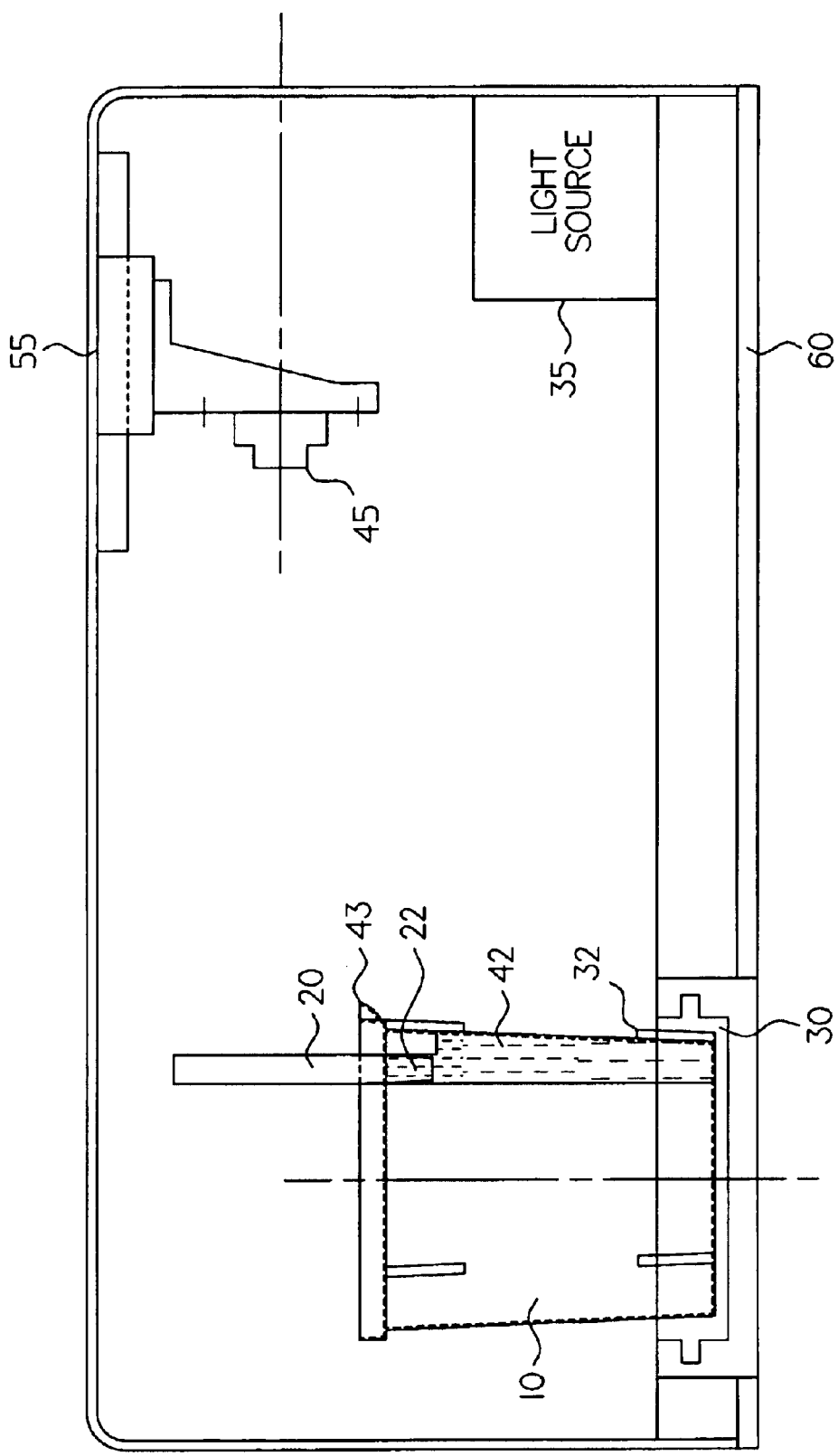
FIG. 2 is a cut-away side plan view of an automatic reader and the test cup taken along 2—2 shown in FIG. 1.

FIG. 2 shows a cut away side plan view of the automated reader platform 60, taken along lines 2—2 shown in FIG. 1. The automated reader platform 60 includes an automated reader 55, a light source 35, a collection cup 10, and a test kit 20. The automated reader 55 includes an imager (camera) 45 and interface circuitry (not shown) which provides operational power to the camera 45 and through which images captured by the camera may be transferred to a video capture card (not shown) in the computer workstation 50. As described below, the workstation 50 analyzes images of the test kit 20 to automatically determine the results of the test. In the exemplary embodiment of the invention, the raw data provided by the reader 55 is automatically stored locally in the workstation 50 and also sent, along with the results of the test, to the central computer (not shown) via the modem (not shown) or other communicating device.

In the exemplary embodiment of the invention, the automated reader 55 may be a BC460 CCD solid-state black and white board camera, available from Ultrak, Carrollton, Texas. Workstation 50 may be, for example, an IBM compatible personal computer running Windows NT with 64 MB of RAM and an image capture board (not shown) that is compatible with the automated reader 55. The modem may, for example, be a conventional 56K modem. Alternatively, the workstation 50 may include a network card through which it connects to a local server which is, in turn, connected to the central computer via a dial-up connection, dedicated wide-area network or a secure Internet connection.

Figure 4:
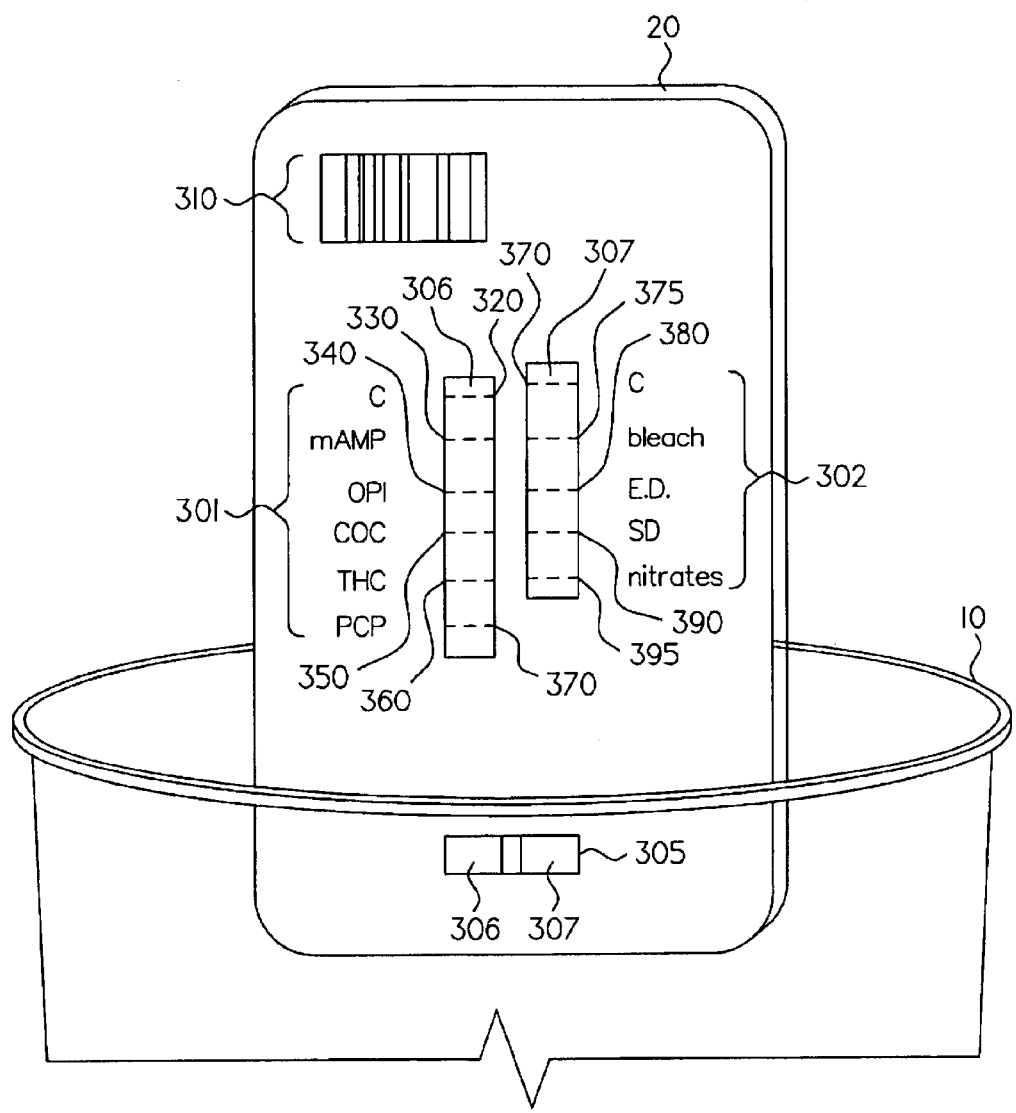
FIG. 4 is a front plan view of an exemplary test kit suitable for use with the present invention.

The collection cup 10 used with the present invention includes a trough 42 adjacent to the pour spout 43 of the cup. After the person being tested has filled the cup, the technician pours a portion of the sample into a separate vial (not shown) which, as described below, may be used to send the sample to a laboratory for further testing. In one embodiment of the invention, the size if the vial is 45 ml. As the technician pours the urine from the cup 10 into the vial, urine flows into the trough 42 until the trough is filled. The upper portion of the trough includes an engagement mechanism 22 which locks the test kit 20 in place in a fixed position in the trough. An exemplary test kit is shown in FIG. 4. As shown in FIG. 4, the test kit includes one or more openings 305 through which the test strips 306 and 307 may be wetted. The engagement mechanism 22 holds the test kit in the trough 42 such that the opening 305 is immersed in urine. In the exemplary embodiment of the invention, the engagement mechanism may be, for example, an opening in the trough having an area slightly smaller than the cross-section of the test kit 20. As the test kit 20 is inserted into the opening, the wall of the trough toward the interior of the cup bends to apply pressure to the back surface of the test kit. The engagement mechanism 22 does not, however, block or otherwise interfere with the opening 305.

In addition, the automated reader platform 60 includes a collection cup holder 30 which is used to place the docked components in a fixed position in the reader platform 60 so that the test kit 20 is in proper position to be read by the camera 45. In the exemplary embodiment of the invention, the cup holder 30 and cup 10 each includes structural features (not shown) which ensure that the cup 10 and the test kit 20 may be inserted only in one location and orientation for imaging by the camera 45.

In the exemplary embodiment of the invention, the test kit may, for example, be a Syva® RapidTest d.a.u.™ test kit which is available from Behring Diagnostics, Inc. or any similar on-site test kit which conforms to the engaging mechanism 22 of the collection cup 10.

In a typical drug screen, the donor brings an authorization form (not shown) containing a client (e.g. employer) bar-code identifier. The technician wands the client bar-code and the workstation 50 assigns a requisition number to the donor. The combination of the client bar-code and a bar-code for the requisition number form a unique identifier for the donor. The workstation 50 then prints out a set of bar-code labels to be applied to all of the consumables in order to associate the consumables uniquely with the donor. Additionally, in response to the wanding of the client bar-code, the workstation displays an electronic form on the monitor of the workstation 50. This form includes fields for information about the person being tested, such as name, address, age and other identifying information. After entering this information, the technician hands the collection cup to the person being tested.

When the person returns with the sample, the technician checks a temperature strip 32 (shown in FIG. 2) on the lower portion of the collection cup 10. In the exemplary embodiment of the invention, the temperature strip 32 includes a series of temperature-sensitive regions (not shown), each of which changes color at a different temperature. The technician may wait until the donor returns with the sample or he may process other donors and, when each donor returns with a sample, wand the bar-code on the cup to bring-up that donor's order form. In either method, the technician then enters the temperature information in a field of the order form.

The technician then pours a portion of the sample from the cup 10 into the collection vial (not shown) thereby filling the trough 42. Next, the technician docks the test kit 20 into the engagement mechanism 22 of the trough 42, immersing the opening 305 of the test kit in the urine sample. The technician then places the integrated cup 10 and test kit 20 into the collection cup holder 30 of the automated reader platform 60, placing the cup 10 and test kit 20 into the reader platform 60 in a fixed position. In the exemplary embodiment of the invention, the cup holder 30 is a drawer which extends from the side of the reader 55 so that a technician may place an integrated cup 10 and test kit 20 into the cup holder 30 and cause the cup holder to be retracted into the reader. In its retracted position, the cup holder 30 holds the test kit in proper orientation for imaging by the automated reader 55.

The technician then signals the workstation 50 through the keyboard 90 that the sample has been inserted. While the automated reader 55 is obtaining the test results, the technician seals the vial and completes the chain of custody documents. The donor is then dismissed.

In response to this signal to begin the test, the workstation 50 obtains and stores an image of the test kit 20 using the reader 55 and the image capture board. The workstation analyzes this first image to ensure that the test kit has been properly integrated into the collection cup 10 and that the collection cup 10 has been properly placed into the cup holder 30. The workstation 50 may, for example, perform this function by checking several the values at several picture element (pixel)-positions, corresponding, for example to specific printed and blank areas on the test kit, for predetermined pixel values. If these values are found, then the test kit is properly aligned. If pixels are not as expected, then the workstation 50 displays a message asking the technician to check the positioning of the test kit 20 in the cup 10 and the positioning of the cup 10 in the platform 60 and to signal the workstation when they have been repositioned. In response to this signal, the workstation 60 repeats the test. After a predetermined number of failures, the workstation signals that the test in inconclusive and instructs the technician to send the vial to the laboratory for further testing. The workstation also sends the identification information on the order form to the central computer so that, at the laboratory, the vial can be associated with the person being tested.

As an alternative to testing specified pixel positions and signalling the technician to re-seat the collection cup, the workstation 50 may correlate the image of obtained from the docked test kit 20 to several different images, each representing a possible displacement of the test kit from a reference position. The image having the highest correlation then defines displacement values relative to the reference position, which are used to obtain data from the image for analysis.

Once the cup is properly seated, the workstation 50 may periodically signal the reader 55 to capture images of the test kit. FIG. 4 shows an exemplary image that may be obtained by the reader 55. This image includes a bar-code 310 which identifies the image of the test kit with a particular individual, and two test strips 306 and 307. Test strip 306 corresponds to an area 301 of the test kit which is examined for the presence of controlled substances such as PCP 370, THC 360, cocaine 350, opiates 340 and methamphetamines 330. Test strip 302 corresponds to an area of the test kit which is examined for the presence of adulterants, that may affect the validity of the test. In the exemplary embodiment of the invention, the adulterants which are identified include bleach 375, electrolyte beverages 380, soft-drinks 390 and riitrites. These controlled substances and adulterants are merely exemplary and do not exclude the testing for other controlled substances and adulterants.

The exemplary test strips also includes control regions 320, labeled with a "C," which change color in the presence of any water-based liquid. These regions are positioned farthest from the opening 305 and indicate that the sufficient urine has been absorbed by the test strips 306 and 307 to provide valid results. In the exemplary embodiment of the invention, the various indicating regions on the test strips 306 and 307 are horizontal bars which are imaged by the reader 55 to have a thickness of approximately 10 pixels and a length of approximately. 100 pixels.

As each of the sequential images is provided by the reader 55, the workstation 60 checks the intensity of predetermined pixel positions corresponding to the control regions 320 to determine when the other regions may be analyzed for controlled substances and adulterants. When an image is captured having a sufficient intensity in the control regions 320, the workstation then analyzes pixel positions in the image which correspond to test regions 330, 340, 350, 360 and 370 for each of the controlled substances and to test regions 375, 380, 390 and 395 which correspond to each of the adulterants. In the exemplary embodiment of the invention, each test region may, for example, be analyzed by averaging intensity values from a predetermined number (e.g. 50) of pixel positions which are positioned near the central portion of the test region. The averaged intensity values obtained by the workstation 60 are then compared to reference values to determine if the test is negative, positive or indeterminate.

In the exemplary embodiment of the invention, a dark-colored bar appears in the region if the test is negative and no bar appears if the test is positive. The intensity of the pixels that are sampled from the bars corresponds to the luminance level of the pixels. Thus a dark pixel has a relatively low intensity value while a bright pixel has a relatively high intensity value.

A common problem in analyzing on-site drug testing kits occurs when a faint bar-appears in any of the regions. The technician must decide whether the faint bar represents a negative, positive or inconclusive result. Different technicians may classify bars with the same intensity differently. The present invention obviates this problem by objectively classifying pixel intensities that are determined under controlled conditions. The exemplary workstation 60 classifies the averaged pixel values as representing a positive, negative or inconclusive result based on whether they are in first, second or third ranges of possible intensity values.

Figure 3:
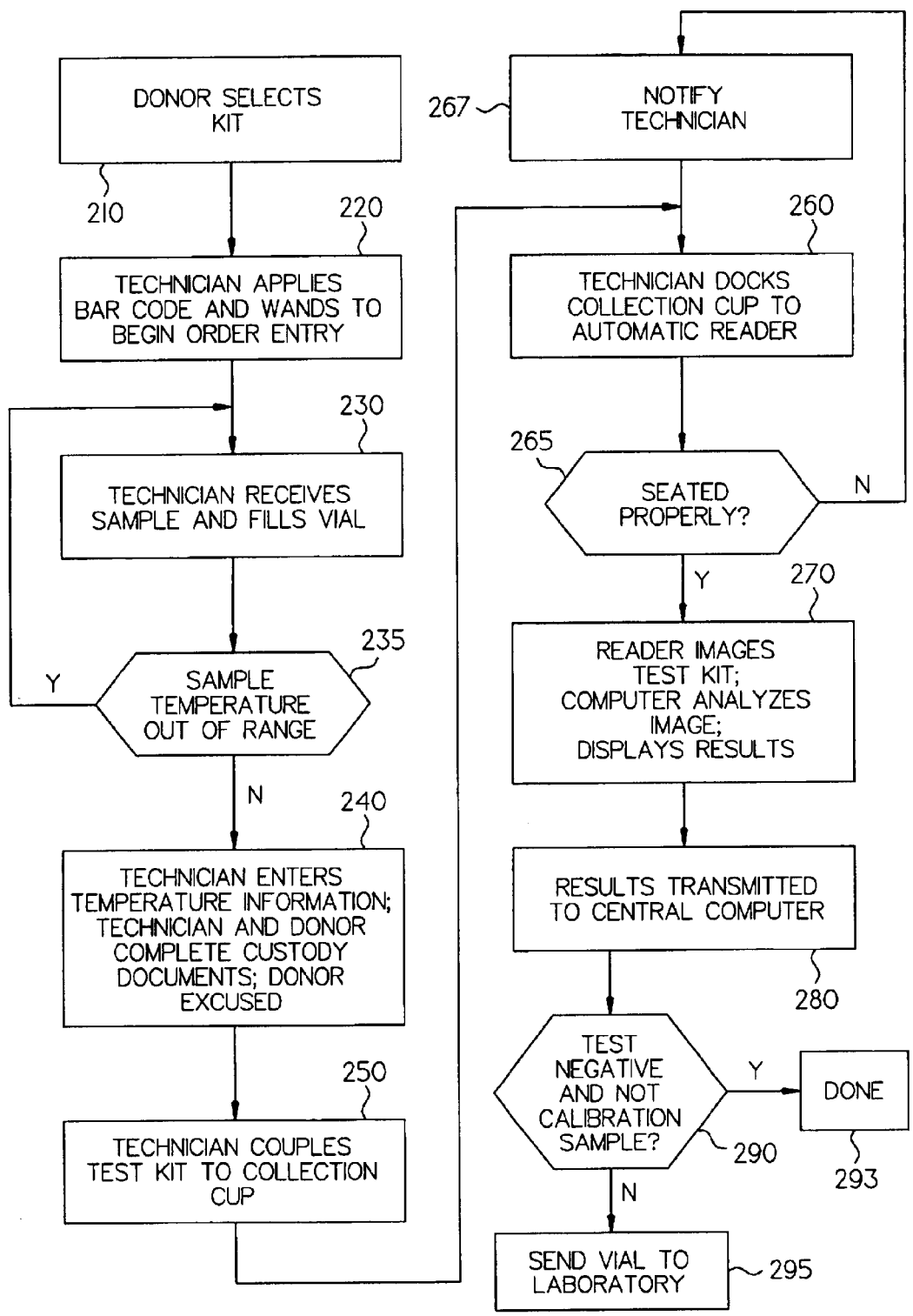
FIG. 3 is a flowchart diagram which presents an overview of the method for on-site drug testing.

FIG. 3 shows an overview of the method for on-site drug testing. First in step 210 the donor receives a collection kit arid a test kit, which is identified with a bar code. Next, in step 220,the technician wands the bar-code to bring up the electronic order form. Also in step 220, the donor and the technician enter identifying and other data into the electronic order entry system. The donor then takes the collection cup 10 and voids. When, at step 230, the technician receives the sample, he checks the temperature sensor 32 on the cup 10 to determine it is consistent with the amount of time since the donor voided. Also, at step 230, the technician pours a portion of the sample into a 45ml vial (not shown), thereby filling the trough 42 of the collection cup 10.

If, as step 230, the temperature of the sample is out of range, the technician may request another sample, in which case, the process branches to step 230, or he may accept the sample and proceed to step 240. At step 240, using keyboard 90, the technician then determines the volume of the sample and enters the volume and temperature data into the donor's order entry form. In step 240 the printer (not shown) which is coupled to the workstation 50 prints out a hard-copy of the custody documents. The donor and the technician then sign the chain of custody documents, including the security seal that is placed over the 45 ml vial and the donor is excused.

In the exemplary embodiment of the invention, the custody documents may be placed on the automated signature reader 70 before they are signed. As the documents are signed, the signatures of the donor and the technician are collected electronically and associated with the order form which is transmitted to the central computer. The documents and the vial are placed in a sealed bag for delivery to the laboratory if necessary, as described below. Because the signatures are captured electronically, they can be matched to the signatures on the chain of custody documents by the central laboratory or by the independent third party.

Continuing with FIG. 3, in step 250 the technician docks the test kit 20 in the engaging mechanism 22 of the trough 42. Once the test kit 20 is docked with the collection cup 10, the urine from the trough will flow into the test kit 20 via capillary action or other similar action. Next, in step 260, the technician places the integrated test kit 20 and collection cup 10 onto the automated reader platform 60. Additionally, in step 260, the technician engages the START indicator on the order form to notify the workstation 60 that the collection cup has been placed in the reader. At step 255, the workstation 50 obtains an image of the test kit, as described above, to determine if the test kit 20 is seated properly in the collection cup 10 and if the collection cup is seated properly in the reader platform 60. If the either of these devices is not seated properly then, at step 257, the workstation 50 asks the technician to check the docking of the test kit 20 in the collection cup 10 and the placement of the collection cup 10 in the reader platform 60. The technician signals the workstation that the collection cup and test kit are properly aligned by activating a button on the order form.

Once the workstation 50 determines that it can obtain an acceptable image of the test kit 20, it may start an internal timer (not shown) to determine when to read the sample. In the exemplary embodiment of the invention, the test kit should provide an acceptable image two minutes after the opening 305 is immersed in the sample. At step 270, when the timer indicates that a valid sample should be available, the workstation 50 captures an image of the test kit and analyzes the image, as described above, to determine the presence of any of the enumerated controlled substances and adulterants.

As an alternative to setting the timer and reading the test kit when the timer expires, the workstation 50 may capture a time sequence of images, recording the results of each sample internally, as described above, until the control regions 320 indicate that the data displayed by the test kit should be valid. In this alternative embodiment of the invention, if the workstation 50 does not attain a valid reading within 10 minutes it declares the test inconclusive.

Once the workstation 50 determines that the reading from the test kit 20 is valid, it analyzes each of the regions on each of the test strips, as described above, and records the results. At step 280, the workstation 50 sends the completed order form and the test results to the central computer, using the modem. At step 290, the workstation determines if the test was positive, indeterminate or, as described below, if the sample is a random sample that is to be laboratory tested in order to verify the proper operation of the collection site. If any of these conditions occurs, the technician, in step 295, is instructed to send the 45 ml vial in a transport bag with the requisition to the central laboratory. The central laboratory then performs confirmatory testing and reports the results through channels that may not include the technician, for example, directly to the personnel department of the company performing the testing.

In addition, it is contemplated that the workstation 50 may not inform the technician of the results of the test and/or may not inform the technician of which samples need to be sent to the central laboratory. In this alternative embodiment, the technician would store all vials as they are produced and, only at the end of a particular batch of tests or at the end of a day of testing, would the workstation generate a list of samples to be sent to the central laboratory.

On each of the test strips 306 and 307 of the test kit 20, the indicating bar for each specific test may vary in thickness and intensity depending on the concentration of the drug and the presence of adulterants in the urine sample. The advantage of using the automated reader 55 and the workstation 50 to automatically read and interpret the results of the test, is that the subjectivity of the reading is eliminated, ensuring that all readings are done quickly, uniformly and fairly. The on-site drug test system further ensures fairness by randomly sending blind samples with known results to the central laboratory for confirmatory testing. In the exemplary embodiment of the invention, every $N^{th}$ sample (e.g. N=40) is sent to the central laboratory for confirmatory testing regardless of whether the interpreted results obtained by the automated reader 55 and workstation 50 were positive or negative.

The on-site drug test system further ensures integrity by periodically re-calibrating the system (e.g. once each day) and by re-calibrating the system for each different batch of test kits. These re-calibration operations may be done at the request of the technician or the workstation 50 may prompt the technician when re-calibration is needed. For example, the workstation may request daily re-calibration before the first test is conducted on any day. This re-calibration may be performed, for example, by placing one or more calibration fixtures, each including an image of a test kit with known intensity levels in the various controlled substance and adulterants, into the platform 60 and signaling the workstation 50 to calibrate itself based on the calibration fixtures. In the exemplary embodiment of the invention, each calibration fixture may contain an identifying code which is read by the automated reader 55 and the workstation 50. Alternatively, the technician may be prompted to enter an identifying code for the fixture.

The on-site drug test system may be re-calibrated for different batches of test kits by having the technician manually enter a re-calibration request when a new batch of test kits is opened or by having the workstation 50 scan for a batch code (not shown) on the image of the test kit as a part of its reading and analysis process. In this alternative embodiment, the workstation may store calibration constants for each of a plurality of test-kit batches or it may prompt the technician to insert one or more test kits from the new batch into respective test solutions of known composition. If the latter method is used, the workstation 50 may analyze the images to generate and store a set of calibration factors for the new batch of test kits. These calibration factors may then be used to normalize any test results obtained using test kits from the identified batch.

Referring back to FIG. 3, in step 280 both the raw data and the interpreted results may be automatically recorded and transmitted to the central computer. The recorded raw data may include, for example, the actual image data for the first valid image of the bars on the test strips; the number of pixels in each bar and the average intensity of each bar; or a losslessly compressed image, (e.g., LWZ) of the bars or of the entire test kit. This raw data may be passed to the central computer for every test or for just the random calibration tests. In addition, the raw image data may be stored locally and used, for example, to re-run a test after a calibration step, when, for example, the test was first run with a test kit from a new batch.

Another embodiment of the on-site drug testing system utilizes the automated reader 55 and the workstation 50 to automatically read and record additional information about the sample. The additional information may include, for exarmple, the temperature from the temperature strip 32, the identifying bar code, the volume of the sample and batch number of the test kit.

The maintenance and calibration of the lab equipment is an important part of the drug testing system. Annual preventive maintenance is performed to ensure that all equipment is functioning properly and to prevent equipment malfunctions. Additionally, the reader 50 is calibrated daily to compensate for the sensitivity of the imager 45 and the variations in the intensity in the light source 35. The calibration is performed by using a test kit 20 and test solution which produces image data having a known intensity. The result of the calibration process can be affected by the distance between the imager 45 of the Reader 50 and the collection cup 10 and by the intensity of the lighting from the light source 35. Consequently, calibration should also be performed whenever a light in the light source 35 is changed and whenever the lot number of the test kit 20 changes.

Figure 5D:
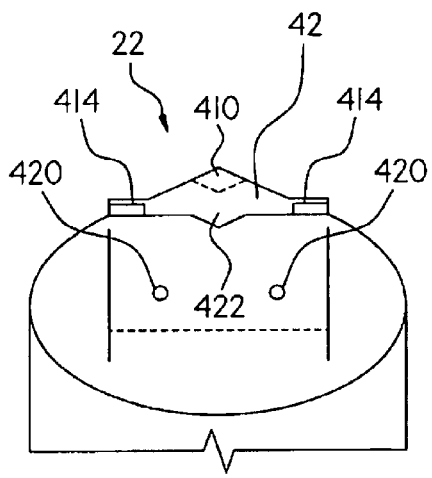
FIG. 5D is a rear perspective view of the upper portion of the collection cup shown in FIG. 5A.
Figure 5A:
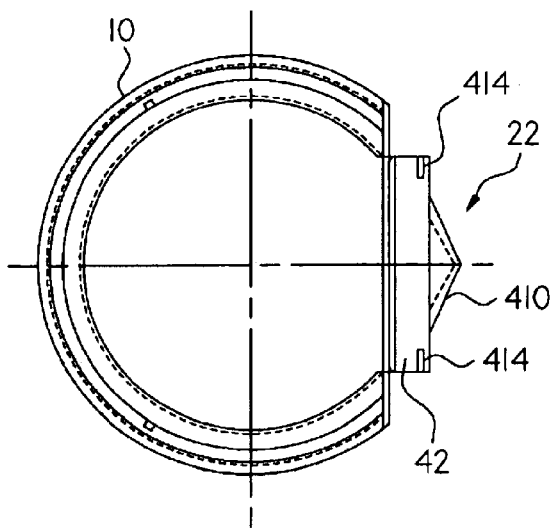
FIG. 5A is a top-plan view of a collection cup suitable for use in the drug testing system shown in FIG. 1.
Figure 5C:
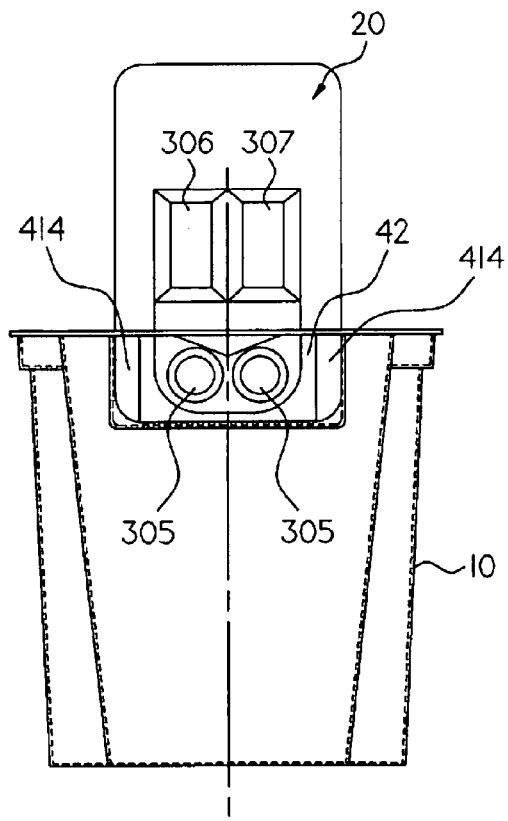
FIG. 5C is a front plan view of the combined test kit and collection kit shown in FIG. 5B.
Figure 5B:
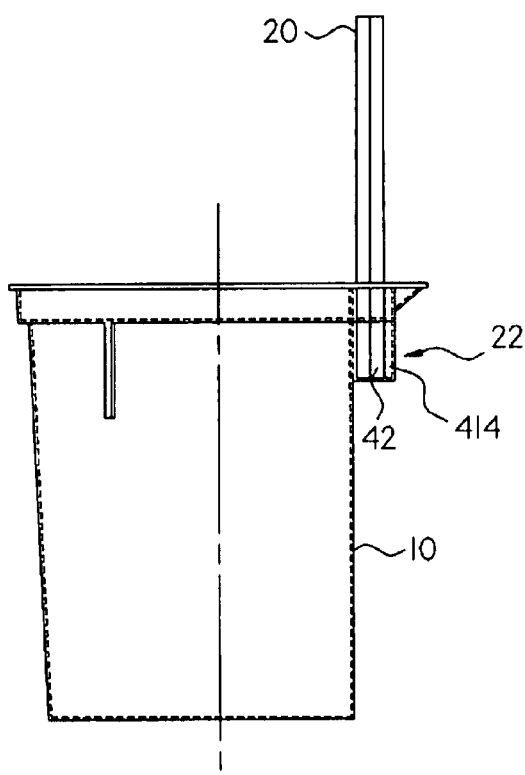
FIG. 5B is a side plan view of a test kit docked with the collection cup shown in FIG. 5A.

FIGS. 5A through 5C illustrate an exemplary collection cup 10 having an engagement mechanism 22 and trough 42 which are suitable for use with the present invention. FIG. 5A is a top plan view of the collection cup 10. The exemplary collection cup has a "D" shaped cross-section except for the portion which includes the trough 42 and pour spout 410. The cup holder 30 of the automated reader platform 60 includes a "D" shaped opening, which matches the cross-section of the bottom of the collection cup. Thus, the cup holder 30 holds the cup 10 in a fixed position such that the docked test kit 20 is held in a predetermined orientation and position within the automated reader platform 60.

The test kit 20 is inserted into the trough 42 and is held in place by the engagement mechanism 22. In the exemplary embodiment, the engagement mechanism 22 includes two locating fingers 414 which extend from the sides of the trough 42. The distance between the back surfaces of the locating fingers 414 and the back of the trough 42 is approximately the same as the thickness of the test kit 20. Thus, when the test kit 20 is inserted in the trough 42, it is held in place by the fingers 414.

FIG. 5B is a side-plan view of the collection cup 10 with the test kit 20 in place. The trough 42 shown in FIGS. 5A through 5D extends down only a small portion of the height of the collection cup 10. Thus, the trough 42 shown in these figures is relatively shallow compared to the trough shown in FIG. 2. As shown in FIG. 5B, the test kit 20 is held in the trough 42 so that the back surface of the test kit engages the back surface of the trough and the sides of the front surface of the test kit engage the two locating fingers 414. When the test kit 20 is inserted in the engagement mechanism, only a small portion of the trough 42, between the fingers 414, holds urine. As shown FIG. 5C, this small portion of the trough is immediately in front of the openings 305 of the test kit 20.

The volume of the trough 42 is designed such that, when the test kit 20 is inserted, the amount of fluid in trough 42 is sufficient to wet the test strips 306 and 307 but does not detrimentally flood the strips 306 and 307. In one embodiment, the volume of the trough is about 110 to 150 microliters. The parameters for designing the amount of urine in the trough include: (a) the number of apertures 420; (b) the size;of each aperture; and (c) the volume of the trough. In one embodiment, when the test kit is inserted in the trough, the apertures are designed (e.g. in number and size) to allow the urine to flow back into the cup 10 at a sufficient rate so as to prevent splashing of the urine. It is desirable to control the amount of urine applied to the test kit in order to produce a predictable test result. FIG. 5D is a perspective rear-view of the collection cup 10 which illustrates features of the cup that enable it to hold the controlled amount of urine.

In the exemplary illustrations of the invention, the rear wall of the trough 42 includes two apertures 420 and a notch 422. As described above, when the technician pours the urine from the collection cup 10 into the vial, the urine flows into the trough 42 through the notch 422 and the apertures 420. As it fills the trough, the urine then flows through the pour spout 410 and into the vial. When the cup 10 is again placed upright, excess urine in the trough flows back into the cup through the apertures 420 to yield the desired controlled amount of urine. In one embodiment, when the test kit 20 is inserted into the trough 42, the test kit blocks the apertures 420, causing the urine in the trough to flow in front of the test kit 20 where it is absorbed by the test strips 306 and 307 through the openings 305 in the front of the test kit 20. In another embodiment, when the test kit 20 is inserted into the trough, the test kit 20 displaces an excess amount of urine and causes this excess urine to flow through the apertures 420 back into the cup 10. Only a measured amount of urine remains in the trough 42 and this is largely absorbed by the test strips 306 and 307 of the test kit 20.

The exemplary collection cup 10 is designed to minimize the technician's potential contact with the urine in the cup. The operation of pouring the urine from the cup into the vial causes a measured amount of urine to flow into the trough 42.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. For example, although the test kit 20 is shown as being docked to the collection kit 10 and then the combined collection cup and test are placed into the reader platform 60, it is contemplated that, once the test kit has been wetted and has produced its result, it may be mounted into the reader platform 60 without the collection cup, in a position such that it can be read by the automated reader 55.

What is claimed:

1. An on-site drug testing system including a network of collection sites, each collection site comprising:

a plurality of integrable consumables including test kits and collection cups for holding samples of bodily fluid, each test kit including at least one optically-readable test strip which produces visible test results when brought into contact with the bodily fluid;

a computer system for transmitting the test results to a central location; and an automated test kit reader, coupled to the computer system, for generating a pixel image of a consumed test kit, including a consumed test strip, the pixel image including a plurality of pixel positions, the plurality of pixel positions including at least one predetermined test pixel position and at least one predetermined control pixel position; when the test strips include a control bar that changes color to indicate sufficient wetting of the consumed test strip by the bodily fluid during consumption of the consumed test strip;

the at least one predetermined control pixel position of the pixel image includes an image of the control bar;

the pixel image is transmitted to the computer system and is automatically analyzed by the computer system by checking intensity of the at least one predetermined control pixel position; and when the intensity of the at least one predetermined control pixel position indicates sufficient wetting of the consumed test strip, the system is configured to check intensity of the at least one predetermined test pixel position of the plurality of pixel positions of the pixel image to generate the test results.

2. An on-site drug testing system according to claim 1, wherein the automated test kit reader includes means for fixing a position of the consumed test kit for imaging the consumed test kit.

3. An on-site drug testing system according to claim 1, wherein the automated test kit reader includes:
an enclosure;
a mechanism in the enclosure for holding a consumed collection cup and the consumed test kit in a predetermined position;
a light source for providing a predetermined level of illumination to the consumed test kit; and
an electronic camera responsive to commands from the computer, the electronic camera for providing the computer system with the pixel image of the consumed test kit which is analyzed by the computer system.

4. An on-site drug testing system according to claim 3, wherein the test strips include indicator bars which change color in response to controlled substances in the bodily fluid and the pixel image generated by the electronic camera including an indicator image of each of the indicator bars.

5. An on-site drug testing system according to claim 4, wherein the consumed test kit and the consumed collection cup each includes an identifying bar-code label and the on-site drug testing system includes a bar-code scanning wand, coupled to the computer system for entering the bar-code information into the electronic test order form.

6. An on-site drug testing system according to claim 4, wherein the indicator image of each of the indicator bars includes at least 10 pixels in its shortest dimension.

7. An on-site drug testing system including a network of collection sites, each collection site comprising:
a plurality of integrable consumables including test kits and collection cups for holding samples of bodily fluid, each test kit including at least one optically-readable test strip having test regions which produces visible test results when brought into contact with the bodily fluid;
a computer system for transmitting the test results to a central location; and
an automated test kit reader, coupled to the computer system, for generating a pixel image of a consumed test kit, including a consumed test strip, the pixel image including a plurality of pixel positions, the plurality of pixel positions including at least one predetermined test region and at least one predetermined control region; wherein
the test strips include a control bar that changes color to indicate sufficient wetting of the consumed test strip by the bodily fluid during consumption of the consumed test strip;
the at least one predetermined control region of the pixel image includes an image of the control bar;
the pixel image of the consumed test strip is transmitted to the computer system and is automatically analyzed by the computer system by analyzing the at least one predetermined control region of the pixel image by averaging intensity values from a predetermined number of pixel positions of said at least one predetermined control region; and
when the averaged intensity of the at least one predetermined control region indicates sufficient wetting of the consumed test strip, the system is configured to analyze the at least one predetermined test region of the pixel image by averaging intensity values from a predetermined number of pixel positions of each of said at least one predetermined test region to generate the test results.

8. An on-site drug testing system including a network of collection sites, each collection site comprising:
a plurality of integrable consumables including test kits and collection cups for holding samples of bodily fluid, each test kit including at least one optically-readable test strip having test regions which produces visible test results when brought into contact with the bodily fluid;
a computer system for transmitting the test results to a central location; and
an automated test kit reader, coupled to the computer system, for generating a pixel image of a consumed test kit, including a consumed test strip, the pixel image including a plurality of pixel positions; wherein
the pixel image is transmitted to and is automatically analyzed by the computer system by checking intensity of a plurality of predetermined test pixel positions of the plurality of pixel positions of the pixel image to generate the test results;
the collection cup includes alignment indicia;
the plurality of predetermined pixel test positions of the pixel image includes a plurality of cup alignment pixels; and
the plurality of cup alignment pixels are configured to be analyzed by the computer system to determine proper positioning of the collection cup.

9. An on-site drug testing system comprising:
a test kit comprising at least one optically-readable test strip, said test strip having a test region which produces visible test results when brought into contact with a bodily fluid, said test strip also having a control region which changes color to indicate sufficient wetting of a consumed test strip by the bodily fluid during consumption of the consumed test strip;
a test kit reader configured to generate a pixel image of a consumed test strip, wherein a test portion of the pixel image corresponds to the test region of the test strip and a control portion of the pixel image corresponds to the control region of the test strip; and
a computer configured to check intensity of the control portion of the pixel image and to check intensity of the test portion of the pixel image, when the intensity of the control portion indicates sufficient wetting of the consumed test strip, to generate the test results.

* * * * *